United States Patent
Weinstein et al.

(10) Patent No.: US 10,466,087 B2
(45) Date of Patent: Nov. 5, 2019

(54) METHOD AND APPARATUS FOR MEASURING A FLUID PARAMETER IN A VIBRATING METER

(75) Inventors: Joel Weinstein, Boulder, CO (US); Mark James Bell, Longmont, CO (US); Andrew Timothy Patten, Boulder, CO (US)

(73) Assignee: Micron Motion, Inc., Boulder, CO (US)

(*) Notice: Subject to any disclaimer, the term of this patent is extended or adjusted under 35 U.S.C. 154(b) by 428 days.

(21) Appl. No.: 13/124,192

(22) PCT Filed: Nov. 13, 2008

(86) PCT No.: PCT/US2008/083387
§ 371 (c)(1),
(2), (4) Date: Apr. 14, 2011

(87) PCT Pub. No.: WO2010/056244
PCT Pub. Date: May 20, 2010

(65) Prior Publication Data
US 2011/0264385 A1    Oct. 27, 2011

(51) Int. Cl.
*G01F 1/84* (2006.01)
*G01N 9/00* (2006.01)

(52) U.S. Cl.
CPC .......... *G01F 1/8436* (2013.01); *G01F 1/8477* (2013.01); *G01N 9/002* (2013.01)

(58) Field of Classification Search
CPC ...... G01F 1/8436; G01F 1/8477; G01N 9/002
USPC .................. 702/45, 48, 54, 100; 73/861.355, 73/861.357, 861.354
See application file for complete search history.

(56) References Cited

U.S. PATENT DOCUMENTS

| | | | |
|---|---|---|---|
| 4,262,523 A * | 4/1981 | Stansfeld | 73/24.05 |
| 5,661,232 A * | 8/1997 | Van Cleve et al. | 73/54.05 |
| 5,734,112 A | 3/1998 | Bose et al. | |
| 6,412,355 B1 | 7/2002 | Haberli et al. | |
| 6,502,466 B1 * | 1/2003 | Cage et al. | 73/861.355 |
| 7,299,705 B2 | 11/2007 | Gysling | |
| 7,716,995 B2 * | 5/2010 | Patten et al. | 73/861.355 |
| 2006/0260384 A1 * | 11/2006 | Gysling et al. | 73/24.01 |
| 2010/0011882 A1 | 1/2010 | Gebhardt et al. | |
| 2010/0198531 A1 * | 8/2010 | Bell | G01F 1/74 702/45 |
| 2010/0275703 A1 * | 11/2010 | McAnally | G01F 1/8495 73/861.357 |

FOREIGN PATENT DOCUMENTS

DE    102007061690 A1    6/2008
JP    2000-505895 A    5/2000
(Continued)

*Primary Examiner* — Alexander Satanovsky
*Assistant Examiner* — Mark I Crohn
(74) *Attorney, Agent, or Firm* — The Ollila Law Group LLC

(57) ABSTRACT

A method for calculating a fluid parameter of a fluid flowing through a vibratory flow meter is provided. The method comprises vibrating the flow meter at one or more frequencies and receiving a vibrational response. The method further comprises generating a first fluid property and generating at least a second fluid property. The method further comprises calculating a fluid parameter based on the first fluid property and the at least second fluid property.

45 Claims, 8 Drawing Sheets

(56) References Cited

FOREIGN PATENT DOCUMENTS

| | | | |
|---|---|---|---|
| RU | 2250438 C1 | 8/2005 | |
| WO | 2000000793 A1 | 1/2000 | |
| WO | 0101086 A1 | 1/2001 | |
| WO | 2006104485 A1 | 10/2006 | |
| WO | WO 2006/104485 A1 * | 10/2006 | ............... G01F 1/84 |
| WO | 2007074055 A1 | 7/2007 | |

* cited by examiner

METHOD AND APPARATUS FOR MEASURING A FLUID PARAMETER IN A VIBRATING METER

TECHNICAL FIELD

The present invention relates to a flow meter, and more particularly, to a method and apparatus for measuring a fluid parameter in a vibrating flow meter.

BACKGROUND OF THE INVENTION

Flow meters are used to measure the mass flow rate, density, and other characteristics of flowing materials. The flowing material may comprise a liquid, gas, solids suspended in liquids or gas, or any combination thereof. Vibrating conduit sensors, such as Coriolis mass flow meters and vibrating densitometers typically operate by detecting motion of a vibrating conduit that contains a flowing material. Properties associated with the material in the conduit, such as mass flow, density and the like, can be determined by processing measurement signals received from motion transducers associated with the conduit. The vibration modes of the vibrating material-filled system generally are affected by the combined mass, stiffness, and damping characteristics of the containing conduit and the material contained therein.

A typical Coriolis mass flow meter includes one or more conduits that are connected inline in a pipeline or other transport system and convey material, e.g., fluids, slurries and the like, in the system. Each conduit may be viewed as having a set of natural vibration modes, including for example, simple bending, torsional, radial, and coupled modes. In a typical Coriolis mass flow measurement application, a conduit is excited in one or more vibration modes as a material flows through the conduit, and motion of the conduit is measured at points spaced along the conduit. Excitation is typically provided by an actuator, e.g., an electromechanical device, such as a voice coil-type driver, that perturbs the conduit in a periodic fashion. Mass flow rate may be determined by measuring time delay or phase differences between motions at the transducer locations. Density of the flow material can be determined from a frequency of a vibrational response of the flow meter. Two such transducers (or pick-off sensors) are typically employed in order to measure a vibrational response of the flow conduit or conduits and are typically located at positions upstream and downstream of the actuator. The two pick-off sensors are generally connected to electronic instrumentation by cabling, such as by two independent pairs of wires. The instrumentation receives signals from the two pick-off sensors and processes the signals in order to derive flow measurements.

One potential source for error in vibrating flow meters is caused by compressibility, also known as velocity of sound effects. These errors generally increase with increasing tube oscillation frequency and therefore, the errors often occur during high frequency operation. A number of models have been developed to characterize the velocity of sound effects in a vibrating flow meter. For example, the error effects in both the measured density and mass flow rate were characterized by Hemp J and Kutin J., Theory of errors in Coriolis flowmeter readings due to compressibility of the fluid being metered. *Flow Measurement and Instrumentation,* 17:359-369 (2006), as:

$$\rho_{vos,err} = \frac{1}{4}\left(\frac{\omega d}{2c}\right)^2 \times 100 \quad (1)$$

$$\dot{m}_{vos,err} = \frac{1}{2}\left(\frac{\omega d}{2c}\right)^2 \times 100 \quad (2)$$

where:
ω=the angular oscillation frequency
d=the inner diameter of the flow tube
c=velocity of sound of the process fluid Therefore, if the velocity of sound in the process fluid is known, the error in the measured density and mass flow rate can be determined and corrected. Prior art solutions have generally addressed the situation where the process fluid comprises a mixture having two or more phases where the velocity of sound of the individual phases is known. For example, PCT patent application PCT/US07/74711, assigned to the present applicant, which is incorporated herein by reference, discloses a method for determining a velocity of sound for a multiphase flow mixture based on known velocity of sounds for the components. It should be understood that the equations listed above as well as the equations provided in the above referenced PCT patent application are merely examples of a model for VOS effects on a vibrating tube. Other models are known and are within the scope of the description and claims. The specific example given above and the examples used throughout should not limit the scope of the present invention.

In many circumstances, for example, if a gaseous mixture has an unknown composition, the velocity of sound may not be known. Furthermore, even if the composition is known, the velocity of sound for those components may be unknown. Other prior art solutions have employed additional sensors, such as acoustic sensors to measure the velocity of sound. This approach is not only more costly, but may be impractical in many situations due to space and cost restrictions.

Therefore, there is a need in the art for a method of obtaining a velocity of sound value based solely on measurements obtained from a vibrating meter. Furthermore, there is a need in the art for obtaining a velocity of sound measurement of a single phase fluid where the components are unknown. The present invention solves this and other problems and an advance in the art is achieved.

ASPECTS

According to an aspect of the invention, a method for calculating a fluid parameter of a fluid flowing through at least a first vibratory flow meter, comprises the steps of:
vibrating the flow meter at one or more frequencies;
receiving a vibrational response;
generating a first fluid property of the fluid;
generating at least a second fluid property of the fluid; and
calculating a fluid parameter based on the first fluid property and the at least second fluid property.

Preferably, the first fluid property and at least second fluid property comprises a first density measurement and at least a second density measurement.

Preferably, the first fluid property and the at least second fluid property comprises a first mass flow rate and at least a second mass flow rate.

Preferably, the step of vibrating the vibratory flow meter comprises the steps of:
vibrating the vibratory flow meter at a first frequency; and
further vibrating the vibratory flow meter at an at least second frequency, with the at least second frequency being a different frequency than the first frequency.

Preferably, the method further comprises the step of separating the vibrational response into a first frequency component of the vibrational response and an at least second frequency component of the vibrational response.

Preferably, the first fluid property is based on a first frequency component of the vibrational response and the at least second fluid property is based on an at least second frequency component of the vibrational response.

Preferably, the step of vibrating the vibratory flow meter comprises the steps of:
vibrating the vibratory flow meter at a first frequency; and
separating the vibrational response into a first frequency component and an at least second frequency component, wherein the first frequency component and the at least second frequency component are generated by the vibration at the first frequency.

Preferably, the method further comprises the steps of:
vibrating at least a second vibratory flow meter;
generating the first fluid property from the first vibratory flow meter; and
generating the at least second fluid property from the at least second vibratory flow meter.

Preferably, the steps of vibrating the first flow meter and the at least second flow meter comprises the steps of:
vibrating the first flow meter at a first frequency; and
vibrating the at least second flow meter at an at least second frequency, with the at least second frequency being different than the first frequency.

Preferably, the first fluid property and at least second fluid property comprises a first density measurement and at least a second density measurement and wherein the first density measurement is generated from a known fluid density.

Preferably, the first fluid property and at least second fluid property comprises a first density measurement and at least a second density measurement and further comprises the steps of:
comparing the first density measurement to an expected density measurement; and
if the difference between the first density measurement and the expected density measurement is less than a threshold value, determining that the first density measurement comprises an actual fluid density.

Preferably, the first fluid property and the at least second fluid property comprises a first mass flow rate and at least a second mass flow rate and further comprises the steps of:
comparing the first mass flow rate to an expected mass flow rate; and
if the difference between the first mass flow rate and the expected mass flow rate is less than a threshold value, determining that the first mass flow rate comprises the actual mass flow rate.

Preferably, the first fluid property and at least second fluid property comprises a first density measurement and at least a second density measurement and further comprises the steps of:
comparing the first density measurement to an expected density; and
if the difference between the first density measurement and the expected density measurement exceeds a threshold value calculating an actual density and a velocity of sound of the fluid.

Preferably, the first fluid property and at least second fluid property comprises a first mass flow rate and at least a second mass flow rate and further comprises the steps of:
comparing the first mass flow rate to an expected mass flow rate; and
if the difference between the first mass flow rate and the expected mass flow rate exceeds a threshold value calculating an actual mass flow rate and a velocity of sound of the fluid Preferably, the fluid parameter comprises a density.

Preferably, the fluid parameter comprises a mass flow rate.

Preferably, the fluid parameter comprises a velocity of sound of the fluid.

Preferably, the method further comprises the step of calculating a density error based on the calculated velocity of sound.

Preferably, the method further comprises the step of correcting the density based on the calculated density error.

Preferably, the method further comprises the step of calculating a mass flow error based on the calculated velocity of sound.

Preferably, the method further comprises the step of correcting a mass flow rate based on the calculated mass flow error.

Preferably, the method further comprises the steps of comparing the calculated velocity of sound to an expected velocity of sound and determining an error condition if the difference between the calculated velocity of sound and the expected velocity of sound exceeds a threshold value.

According to another aspect of the invention, a vibratory flow meter for calculating a fluid parameter of a flowing fluid, comprising a meter assembly including vibratory sensors and meter electronics coupled to the vibratory sensors, with the vibratory flow meter being characterized by:
the meter electronics being configured to:
receive a vibrational response from the vibratory sensors;
generate a first fluid property of the fluid;
generate at least a second fluid property of the fluid; and
calculate a fluid parameter based on the first fluid property and the at least second fluid property.

Preferably, the first fluid property and at least second fluid property comprises a first density measurement and at least a second density measurement.

Preferably, the first fluid property and the at least second fluid property comprises a first mass flow rate and at least a second mass flow rate.

Preferably, the first fluid property is based on a first frequency component of the vibrational response and the at least second fluid property is based on at least a second frequency component of the vibrational response.

Preferably, the meter electronics is further configured to vibrate the vibratory flow meter at a first frequency and at an at least second frequency, with the at least second frequency being a different frequency than the first frequency.

Preferably, the meter electronics is further configured to separate the vibrational response into a first frequency component and an at least second frequency component.

Preferably, the meter electronics is further configured to vibrate the flow meter at a first frequency and separate the vibrational response into a first frequency component and an at least second frequency component, wherein the first frequency component and the at least second frequency component are generated by the vibration at the first frequency.

Preferably, the first fluid property and at least second fluid property comprises a first density measurement and at least a second density measurement wherein the first density measurement is generated from a known fluid density.

Preferably, the first fluid property and at least second fluid property comprises a first density measurement and at least a second density measurement and with the meter electronics being further configured to compare the first density measurement to an expected density and if the difference between the first density measurement and the expected density is less than a threshold value, determine that the first density measurement comprises an actual density.

Preferably, the first fluid property and at least second fluid property comprises a first mass flow rate and at least a second mass flow rate and with the meter electronics being further configured to compare the first mass flow rate to an expected mass flow rate and if the difference between the first mass flow rate and the expected mass flow rate is less than a threshold value, determine that the first mass flow rate comprises an actual mass flow rate.

Preferably, the fluid parameter comprises a density.

Preferably, the fluid parameter comprises a mass flow rate.

Preferably, the fluid parameter comprises a velocity of sound of the fluid.

Preferably, the meter electronics is further configured to calculate a density error based on the calculated velocity of sound.

Preferably, the meter electronics is further configured to correct a density based on the density error.

Preferably, the meter electronics is further configured to calculate a mass flow error based on the calculated velocity of sound.

Preferably, the meter electronics is further configured to correct a mass flow rate based on the mass flow error.

Preferably, the meter electronics is further configured to compare the calculated velocity of sound to an expected velocity of sound and determine an error if the difference between the calculated velocity of sound and the expected velocity of sound exceeds a threshold value.

According to another aspect of the invention, a vibratory flow meter system for calculating a fluid parameter of a flowing fluid, comprising a first flow meter and at least a second flow meter and a processing system coupled to the first flow meter and the at least second flow meter, with the vibratory flow meter system being characterized by:
  the processing system being configured to:
  receive a first vibrational response from the first flow meter and receive at least a second vibrational response from the at least second flow meter;
  generate a first fluid property of the fluid based on the first vibrational response;
  generate at least a second fluid property of the fluid based on the at least second vibrational response; and
  calculate a fluid parameter based on the first fluid property and the at least second fluid property.

Preferably, the first fluid property and at least second fluid property comprises a first density measurement and at least a second density measurement.

Preferably, the first fluid property and the at least second fluid property comprises a first mass flow rate and at least a second mass flow rate.

Preferably, the processing system being further configured to vibrate the first flow meter at a first frequency and vibrate the at least second flow meter at an at least second frequency, with the at least second frequency being different than the first frequency.

Preferably, the first fluid property and at least second fluid property comprises a first density measurement and at least a second density measurement and wherein the first density measurement is generated from a known fluid density.

Preferably, the first fluid property and at least second fluid property comprises a first density measurement and at least a second density measurement and with the processing system being further configured to:
  compare the first density measurement to an expected density measurement; and
  determine that the first density measurement comprises an actual fluid density if the difference between the first density measurement and the expected density measurement is less than a threshold value.

Preferably, the first fluid property and at least second fluid property comprises a first density measurement and at least a second density measurement and with the processing system being further configured to:
  compare the first density measurement to an expected density; and
  calculate an actual density and a velocity of sound of the fluid if the difference between the first density measurement and the expected density measurement exceeds a threshold value.

Preferably, the first fluid property and at least second fluid property comprises a first mass flow rate and at least a second mass flow rate and with the processing system being further configured to:
  compare the first mass flow rate to an expected mass flow rate; and
  determine that the first mass flow rate comprises an actual mass flow rate if the difference between the first mass flow rate and the expected mass flow rate is less than a threshold value.

Preferably, the first fluid property and at least second fluid property comprises a first mass flow rate and at least a second mass flow rate and with the processing system being further configured to:
  compare the first mass flow rate to an expected mass flow rate; and
  calculate an actual mass flow rate and a velocity of sound of the fluid if the difference between the first mass flow rate and the expected mass flow rate exceeds a threshold value.

Preferably, the fluid parameter comprises a density.

Preferably, the fluid parameter comprises a mass flow rate.

Preferably, the fluid parameter comprises a velocity of sound.

Preferably, the processing system is further configured to calculate a density error based on the calculated velocity of sound.

Preferably, the processing system is further configured to correct a density based on the calculated density error.

Preferably, the processing system is further configured to calculate a mass flow error based on the calculated velocity of sound.

Preferably, the processing system is further configured to correct a mass flow rate based on the calculated mass flow error.

Preferably, the processing system is further configured to compare the calculated velocity of sound to an expected velocity of sound and determine an error if the difference between the calculated velocity of sound and the expected velocity of sound exceeds a threshold value.

DETAILED DESCRIPTION OF THE INVENTION

FIGS. 1-8 and the following description depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

Figure 1:
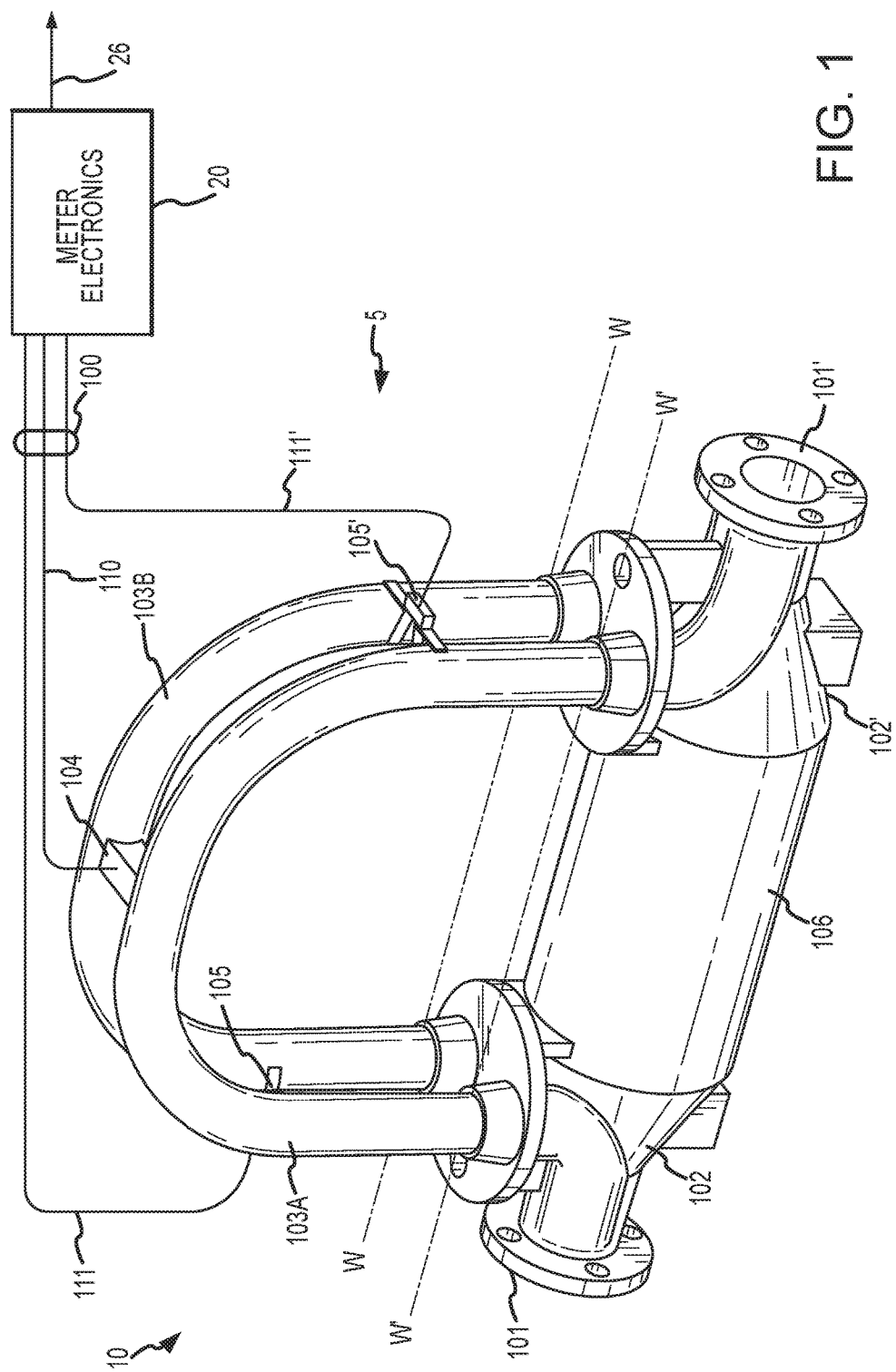
FIG. 1 shows a vibratory meter comprising a flow meter assembly and meter electronics.

FIG. 1 shows a vibrating meter 5 comprising a flow meter assembly 10 and meter electronics 20. The meter electronics 20 is connected to the meter assembly 10 via leads 100 and is configured to provide measurements of one or more of a density, mass flow rate, volume flow rate, totalized mass flow, temperature, velocity of sound, viscosity, phase composition, and other information over a communication path 26. It should be apparent to those skilled in the art that the present invention can be used in any type of Coriolis flow meter regardless of the number of drivers, pick-off sensors, flow conduits, or the operating mode of vibration. In addition, it should be recognized that the flow meter 5 may alternatively comprise a vibratory flow meter that lacks the mass flow measurement capabilities of a Coriolis flow meter, such as a vibratory densitometer.

The flow meter assembly 10 includes a pair of flanges 101 and 101', manifolds 102, 102', vibratory sensors including a driver 104 and pick-off sensors 105, 105', and flow conduits 103A and 103B. The driver 104 and pick-off sensors 105 and 105' are connected to the flow conduits 103A and 103B.

The flanges 101 and 101' are affixed to the manifolds 102 and 102'. The manifolds 102 and 102' can be affixed to opposite ends of a spacer 106. The spacer 106 maintains the spacing between the manifolds 102 and 102' in order to prevent undesired vibrations in the flow conduits 103A and 103B. When the flow meter assembly 10 is inserted into a conduit system (not shown) which carries the flow material being measured, the flow material enters the flow meter assembly 10 through the flange 101, passes through the inlet manifold 102 where the total amount of flow material is directed to enter the flow conduits 103A and 103B, flows through the flow conduits 103A and 103B and back into the outlet manifold 102', where it exits the meter assembly 10 through the flange 101'.

The flow conduits 103A and 103B are selected and appropriately mounted to the inlet manifold 102 and to the outlet manifold 102' so as to have substantially the same mass distribution, moments of inertia, and elastic modules about the bending axes W-W and W'-W' respectively. The flow conduits 103A and 103B extend outwardly from the manifolds 102 and 102' in an essentially parallel fashion.

The flow conduits 103A and 103B are driven by the driver 104 in opposite directions about the respective bending axes W and W' and at what is termed the first out of phase bending mode of the flow meter 5. The driver 104 may comprise one of many well known arrangements, such as a magnet mounted to the flow conduit 103A and an opposing coil mounted to the flow conduit 103B. An alternating current is passed through the opposing coil to cause both conduits to oscillate. A suitable drive signal is applied by the meter electronics 20 to the driver 104 via the lead 110.

The meter electronics 20 can generate a drive signal at a predetermined frequency. The meter electronics 20 can generate a drive signal at varying frequencies, including generating multiple superimposed frequencies.

The meter electronics 20 receives sensor signals on the leads 111 and 111', respectively. The meter electronics 20 produces a drive signal on the lead 110 which causes the driver 104 to oscillate the flow conduits 103A and 103B. The meter electronics 20 processes the left and right velocity signals from the pick-off sensors 105 and 105' in order to compute a mass flow rate. In some embodiments, the meter electronics 20 can process signals received from the driver 104 to compute a mass flow rate. The communication path 26 provides an input and an output means that allows the meter electronics 20 to interface with an operator or with other electronics systems. The description of FIG. 1 is provided merely as an example of the operation of a Coriolis flow meter and is not intended to limit the teaching of the present invention.

Advantageously, available low frequency vibratory flow meters can accurately measure density where the negative effects from the velocity of sound are not excessive. Therefore densities obtained from low frequency vibratory flow meters, as is generally known in the art, can typically be assumed to comprise accurate values. Conversely, high frequency meters are available that accurately measure a frequency of vibration of the meter but are encumbered by additional errors caused by velocity of sound effects on density measurements. These two characteristics are advantageously employed to accurately and reliably determine densities and other flow characteristics.

Figure 2:
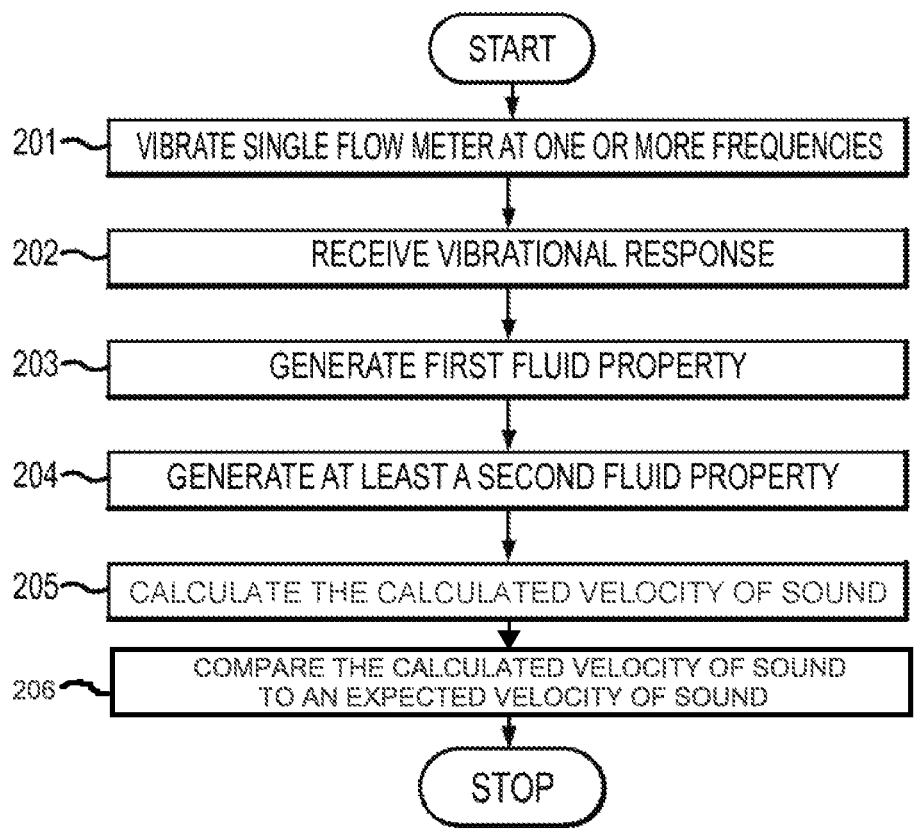
FIG. 2 is a flowchart of a method for calculating a velocity of sound in a fluid flow according to an embodiment of the invention.

FIG. 2 shows a flowchart 200 of a method for calculating a fluid parameter of a fluid according to an embodiment of the invention. The fluid parameter may comprise, but is not limited to, a velocity of sound, a mass flow rate, or a density. The discussion below often refers to the fluid parameter as comprising a velocity of sound. It should be appreciated that this is merely one example and the present invention is not limited to the specific embodiments discussed. In step 201, a flow meter assembly of a vibratory flow meter is vibrated. Only a single vibratory flow meter is needed for this embodiment of the invention. The flow meter assembly may be vibrated at one or more frequencies.

In one embodiment of the invention, the flow meter assembly is vibrated at a single drive frequency. The single drive frequency can generate a vibrational response including the first frequency component and at least a second frequency component, as the vibration of the meter assembly at the single drive frequency can induce multiple frequency response components. For example, noise created by flow through the flow meter will generally create vibration in the flow meter assembly at least a second frequency. The at least second frequency will generally be a frequency different than the drive frequency. This at least second frequency component of the vibrational response will generally be much smaller in amplitude than the first frequency component. However, the at least second frequency component can be amplified and processed. The first vibrational frequency response and the at least second vibrational frequency response can subsequently be processed in the steps below.

In another embodiment, the flow meter assembly of the single flow meter is vibrated at a first drive frequency and is also vibrated at an at least second drive frequency. The at least second drive frequency is different than the first drive frequency. According to an embodiment of the invention, the first drive frequency comprises a low frequency and the at least second drive frequency comprises a higher drive frequency. It should be understood that the single vibratory flow meter may need to be calibrated for both the first drive frequency and the at least second drive frequency. The single vibratory flow meter may be calibrated using both air and water, for example. The first and second drive frequencies generate a vibrational response comprising a first frequency component and at least a second frequency component. It should be appreciated that the more drive frequencies utilized, the more vibrational responses obtained. Therefore, in some embodiments, more than two drive frequencies are utilized to increase the accuracy of the calculated fluid parameter.

In another embodiment of the invention, the flow meter assembly is vibrated at the first drive frequency and then at the at least second drive frequency. Alternatively, the flow meter may be simultaneously vibrated at both the first drive frequency and the at least second drive frequency. This can be accomplished if the drive signal comprises a composite of the two or more frequencies, for example. As a result, a vibrational response of the flow meter includes at least two component frequencies.

In all of the above embodiments, the single vibratory flow meter produces a vibrational response. In some embodiments, the vibrational response comprises a first frequency component and at least a second frequency component. However, it should be appreciated that if the vibratory flow meter is vibrated at only a higher drive frequency, the vibrational response may comprise only a single frequency component. The vibrational response can subsequently be processed in the steps below.

In step 202, the vibrational response is received from the single vibratory flow meter. The vibrational response may be received from the pick-off sensors 105A, 105B, or alternatively from the driver 104. The vibrational response can include the first frequency component and the at least second frequency component. The at least second frequency component comprises a different frequency than the first frequency component. For example, as discussed above, the at least second frequency component can comprise a higher frequency than the first frequency component. The vibrational response can be processed to obtain the first frequency component and the at least second frequency component. The processing can comprise separating the vibrational response into the first frequency component and the at least second frequency component. The processing can comprise separating the vibrational response into the first frequency component and the at least second frequency component, such as through the use of band-pass filters, for example.

In step 203, a first fluid property is generated. The first fluid property may comprise a density, a mass flow rate, a volume flow rate, a viscosity, etc. This list is not exhaustive and those skilled in the art will readily recognize additional fluid properties that may be generated. The discussion below refers to the first fluid property as comprising a density measurement solely for the purpose of clarity and should in no way limit the scope of the invention. According to an embodiment of the invention, the first density measurement is generated using a first frequency derived from the first frequency component. According to another embodiment of the invention, the first density measurement is generated from a stored or a known density value. According to an embodiment of the invention, the first density measurement is assumed to comprise the actual density of the flowing material. It should be understood that the term "actual" density is meant to mean the density that would be obtained if there were no velocity of sound errors. Therefore, although the term actual density is used, the calculated actual density may still contain errors caused by other variables and therefore could vary from the true density. The assumption that the first density measurement comprises the actual density is generally accurate when the first frequency comprises a frequency low enough that the velocity of sound effects that create errors in the density measurements are relatively small and therefore have little, if any, impact. However, in certain applications this may not be a realistic assumption. Therefore, the first density measurement may be compared to an expected density stored or obtained from a lookup table, for example and discarded if the difference between the first density measurement and an expected density measurement exceeds a threshold value. Alternatively, if the difference between the first density measurement and the expected density measurement exceeds the threshold value, multiple equations may be used to calculate the velocity of sound rather than a single equation. This is explained in more detail below. The threshold value may be a stored value or may be input from a user/operator. Alternatively, the threshold value may be based on the user/operator's desire for an accurate measurement. Furthermore, the expected density may be a stored value or may be input from a user/operator. Alternatively, the expected density may be based on previous measurements. In other embodiments, the first density measurement may be generated from the stored or known value. In other words, the first density measurement does not need to be generated from the first frequency component.

In step 204, at least a second fluid property is generated. The at least second fluid property may comprise a density, a mass flow rate, a volume flow rate, a viscosity, etc. This list is not exhaustive and those skilled in the art will readily recognize additional fluid properties that may be generated. The at least second fluid property may comprise the same fluid property as the first fluid property or may comprise a different fluid property. The at least second fluid property is described below as comprising a density measurement solely for the purpose of clarity and should in no way limit the scope of the invention. According to an embodiment of the invention, the at least second density measurement is generated using an at least second frequency of the at least second frequency component. As discussed above, according to an embodiment of the invention, the at least second frequency is a different frequency than the first frequency. Consequently, due to vibration of the flow material at different frequencies, and the resulting velocity of sound effects, the first density measurement and the at least second density measurement will differ. This may be true for example, when the first density measurement comprises the actual density and the second density measurement is obtained at a higher frequency where the density measurement contains errors due to velocity of sound effects. These differences can be used to determine various fluid parameters using a variety of models. The fluid parameter may comprise, for example, a velocity of sound, a density, or a mass flow rate. It should be appreciated that the models provided below are merely examples and those skilled in the art will readily recognize various additional models that are capable of measuring additional fluid parameters. One example model is provided in equation (3).

$$\begin{bmatrix} 1 & \frac{1}{4}\left(\frac{\omega_1 d}{2}\right)^2 \\ 1 & \frac{1}{4}\left(\frac{\omega_2 d}{2}\right)^2 \\ \vdots & \vdots \\ 1 & \frac{1}{4}\left(\frac{\omega_n d}{2}\right)^2 \end{bmatrix} \begin{Bmatrix} \rho_{actual} \\ \beta \end{Bmatrix} = \begin{Bmatrix} \rho_1 \\ \rho_2 \\ \vdots \\ \rho_n \end{Bmatrix} \quad (3)$$

Where: $\beta = \frac{\rho_{actual}}{c^2}$

Using a matrix such as shown in equation (3) various fluid parameters may be determined. The specific number of fluid parameters determined may depend, for example, on the number of vibrational frequencies utilized. In the matrix provided, each frequency that the flow meter is vibrated at can provide another equation. It should be appreciated that while the discussion is limited to determining an actual density and a velocity of sound of the fluid using a first and at least a second density measurement, other fluid parameters may be determined simply by vibrating the flow meter at more frequencies or using other mathematical models. For example, in some embodiments, such as when the fluid comprises a gas, the density measurements may not provide adequate resolution. However, mass flow measurements may provide adequate resolution. Therefore, rather than utilizing a density measurement, a mass flow measurement may be utilized based on equation (2). This would result in a model such as shown by equation (4):

$$\begin{bmatrix} 1 & \frac{1}{2}\left(\frac{\omega_1 d}{2}\right)^2 \\ 1 & \frac{1}{2}\left(\frac{\omega_2 d}{2}\right)^2 \\ \vdots & \vdots \\ 1 & \frac{1}{2}\left(\frac{\omega_n d}{2}\right)^2 \end{bmatrix} \begin{Bmatrix} \dot{m}_{actual} \\ \beta \end{Bmatrix} = \begin{Bmatrix} \dot{m}_1 \\ \dot{m}_2 \\ \vdots \\ \dot{m}_n \end{Bmatrix} \quad (4)$$

where $\beta = \frac{\dot{m}_{actual}}{c^2}$.

Therefore, the matrix (4) can be utilized in a similar manner as matrix (3).

In step 205, the fluid parameter of the flowing material is determined based on the first density measurement and the at least second density measurement. According to an embodiment of the invention, the fluid parameter can comprise a velocity of sound, for example. The discussion below often refers to the fluid parameter as comprising the velocity of sound solely as an example. Therefore, the present invention should not be limited to velocity of sound calculations. According to an embodiment of the invention, the velocity of sound for the flowing material can be determined using equation (5).

$$\frac{\rho_{second} - \rho_{first}}{\rho_{first}} = \frac{1}{4}\left(\frac{\omega_{second} d}{2c}\right)^2 \quad (5)$$

where:
$\rho_{first}$=the first density measurement
$\rho_{second}$=the second density measurement
$\omega_{second}$=the at least second frequency
d=inner diameter of the flow tube 103A, 103B
c=velocity of sound of the flowing material According to an embodiment of the invention, if the first density measurement is considered to comprise the actual density, i.e., the difference between the first density measurement and the expected density measurement is within the threshold value, then equation (5) can be used on its own to solve for the velocity of sound of the flowing material. As mentioned above, in some embodiments, the first density measurement is generated based on a known or stored density measurement. Therefore, the first density measurement does not need to be generated based on the first frequency component of the vibrational response. The first density measurement may be input by a user/operator or retrieved from a memory or the like. Everything in equation (5) except for the velocity of sound can be measured using the first frequency component and the at least second frequency component as discussed above. Therefore, the velocity of sound for the flowing material can be calculated based on the first density measurement, obtained from the first frequency, and the at least second density measurement, obtained from the at least second frequency. Using the first and at least second density measurements, a calculation of the velocity of sound can be generated using a single vibratory flow meter without requiring external measuring devices as in the prior art. Alternatively, more than one flow meter may be used as discussed below. It should be appreciated that although equation (5) can be used whenever desired, it provides the most accurate calculation when the difference between the first density measurement and the actual density of the fluid is within a threshold value. As discussed above, this is a reasonable assumption if the velocity of sound effects does not create a substantial error in the density obtained at the first frequency. Furthermore, it should be appreciated that equation (5) is merely one example model equation and other models are contemplated and are within the scope of the invention. Therefore, other fluid parameters may be calculated.

In certain situations, it is not reasonable to assume that the first density measurement comprises the actual fluid density. Therefore, according to an embodiment of the invention, if the difference between the first density measurement and the actual density exceeds a threshold value, two equations can be used to solve for a fluid parameter. According to an embodiment of the invention, the fluid parameter may comprise the actual fluid density. According to another embodiment of the invention, the fluid parameter may comprise the velocity of sound. According to another embodiment of the invention, the fluid parameter may comprise the actual mass flow rate. It should be understood that the term "actual" mass flow rate is meant to mean the mass flow rate that would be obtained without velocity of sound effects.

$$\frac{\rho_{first} - \rho_{actual}}{\rho_{actual}} = \frac{1}{4}\left(\frac{\omega_{first} d}{2c}\right)^2 \qquad (6)$$

$$\frac{\rho_{second} - \rho_{actual}}{\rho_{actual}} = \frac{1}{4}\left(\frac{\omega_{second} d}{2c}\right)^2 \qquad (7)$$

Therefore, equations (6) and (7) may be used in combination when the first density measurement is not believed to be the actual density or in situations where the actual density is unknown. This may be determined for example if the difference between the first density measurement and the expected density measurement exceeds a threshold difference, for example. This may also be true if the vibrating meter is considered to be a high frequency meter where the velocity of sound effect on the density readings produces excessive errors even at the first frequency.

Therefore, it should be appreciated that according to another embodiment of the invention, the calculated velocity of sound can be used to compensate for velocity of sound effects in higher frequency meters. For example, if the velocity of sound is calculated for a given fluid at a given temperature using equation (5) then, this calculated velocity of sound can be utilized in higher frequency meters to compensate for density or mass flow rate errors due to the velocity of sound effects using equations (1) and (2), for example. However, in order to do so in a high frequency meter, either the actual fluid density may need to be known or both equations (6) and (7) may need to be utilized. This provides two equations for two unknowns (velocity of sound for the fluid and the actual density measurement). Therefore, the velocity of sound effects in a high frequency meter may now be compensated using the method according to the present invention. It should be understood that the present invention is not limited to equations (6) and (7), but rather, persons skilled in the art will readily recognize other similar equations that may be used to calculate other fluid parameters using a first density measurement and at least a second density measurement.

The calculated velocity of sound may be utilized for a variety of purposes. According to one embodiment of the invention, the calculated velocity of sound may be utilized in conjunction with equations (1) and (2), for example to calculate an error in future density and mass flow measurements. This is especially useful in embodiments where the flow meter is operated at a drive frequency high enough to cause errors in the density and mass flow rate measurements due to velocity of sound effects.

The present invention has been described in conjunction with a vibratory meter. Although the discussion above has been primarily directed towards a Coriolis flow meter, it should be understood that in many embodiments, the invention can be utilized with other vibratory meters that do not include the capabilities of a Coriolis flow meter. For example, the vibratory meter may comprise a vibrating densitometer, for example. However, there may be times when mass and/or volume flow rates may be desired. Therefore, there may be situations where a Coriolis mass flow meter is implemented but the mass flow rate capabilities are only used on occasion. By calculating the velocity of sound of the fluid, the present invention can calculate a mass flow rate as well. This is especially accurate for compressible fluids, such as gases.

It should be appreciated that the present invention can be utilized for a number of purposes once the velocity of sound for the fluid has been determined. For example, in gases, two variables that are often difficult to determine are the specific heat ratio of the gas, k, and the individual gas constant of the components, R. Two equations for gas that are often useful are the velocity of sound in an ideal gas and the ideal gas equation:

$$c = \sqrt{kRT} \qquad (8)$$

where:
k=specific heat ratio of the gas
R is the individual gas constant of the components
T is the temperature $$P = \rho RT \qquad (9)$$

where:
P=pressure
$\rho$=actual fluid density

Advantageously, in many vibrating flow meters, the temperature is a known variable. Therefore, once the velocity of sound is determined, the remaining variables can be easily calculated. These two equations can often be used separately or in combination once the velocity of sound is known to determine any number of properties of the system, such as for example the mixture molecular weight, the efficiency of a compressor, measurement correction, etc. The particular examples should not in any way limit the scope of the invention, but are provided solely to aid in the understanding of the utility of the present invention and provide examples of how the calculated velocity of sound may be utilized.

One particular advantage of the above mentioned method is that the velocity of sound of the fluid in the vibratory meter can be monitored for changes. A change in the velocity of sound for the fluid may be indicative of a number of conditions. According to an embodiment of the invention, a calculated velocity of sound for the fluid may be compared to a previously calculated velocity of sound. The comparison may be used as a diagnostic for determining a change in fluid composition, for example. In other embodiments, the comparison may be used to determine a change in fluid phase, for example.

In Coriolis flow meter applications, it is well known that a change in fluid phase, for example entrained gas in a fluid, can be determined based on a change in the drive gain. However, in order for the drive gain to be affected, the amount of entrained gas may need to be above a certain threshold amount. The particular threshold value may depend on the conditions and fluids monitored. The present applicant has determined that a much lower level of entrained gas can be detected by monitoring changes in the velocity of sound for the fluid.

Generally, the velocity of sound for a liquid is greater than the velocity of sound for a gas of the same composition. However, the velocity of sound of a mixed phase is generally lower than either of the pure phases. For many compositions, the velocity of sound drops dramatically when the fluid comprises one phase with small amounts of an entrained second phase, for example a liquid with small amounts of entrained gas, or alternatively, a liquid or gas with entrained solids, or a gas with entrained liquid droplets. One of the main reasons is because the compressibility dramatically changes while the mixture density remains relatively constant. Therefore, the velocity of sound for the fluid can be determined according to one of the methods outlined in the present application and compared to an expected velocity of sound. If the difference between the calculated velocity of sounds and the expected velocity of sound is greater than a threshold value, the meter electronics 20, or alternatively, a user/operator may determine an error. The error may comprise determining that the fluid composition and/or fluid phase has changed, for example. The expected velocity of sound may be based on a previously calculated velocity of sound or it may be obtained from a lookup table, a value stored in a memory, a user/operator input, etc.

It should be appreciated that although the comparison as described above compares a first calculated velocity of sound to at least a second velocity of sound, the comparison may be made between a calculated velocity of sound for the fluid and an expected velocity of sound. Therefore, only one calculation needs to be made in order to perform the diagnostic discussed above.

The mass or volume flow rates can be calculated once the velocity of sound is calculated using equation (10), which provides a density ratio between the density in the flow tube 103A, 103B and the stagnation density:

$$\frac{\rho}{\rho_o} = \left[\frac{1}{1+\left(\frac{k-1}{2}\right)Ma^2}\right]^{\frac{1}{k-1}} \quad (10)$$

where:
ρ=density within flow tube
$\rho_o$=stagnation density
k=specific heat ratio of the gas (calculated from equation (8) or (9) above)
Ma=Mach number Equation (10) can therefore be used to calculate the Mach number, which is also defined as:

$$Ma = \frac{V}{c} \quad (11)$$

Where V is the fluid velocity. Therefore, because the velocity of sound is already known, the volumetric flow rate $\dot{Q}$ can be calculated if the flow tube area is known based on equations (11) and (12).

$$\dot{Q}=A*V \quad (12)$$

Where A is the flow tube area. Because the density is also known, the mass flow rate can also be calculated as is generally known in the art.

Therefore, the present invention allows a mass and/or volume flow rate to be calculated using a vibrating densitometer based on a calculated velocity of sound of the fluid.

As discussed above, the present invention requires generating first and at least second density measurements. The first and at least second density measurements can be based on first and at least a second frequency response. Below is a discussion of how the frequency responses are generated according to an embodiment of the invention.

Figure 3:
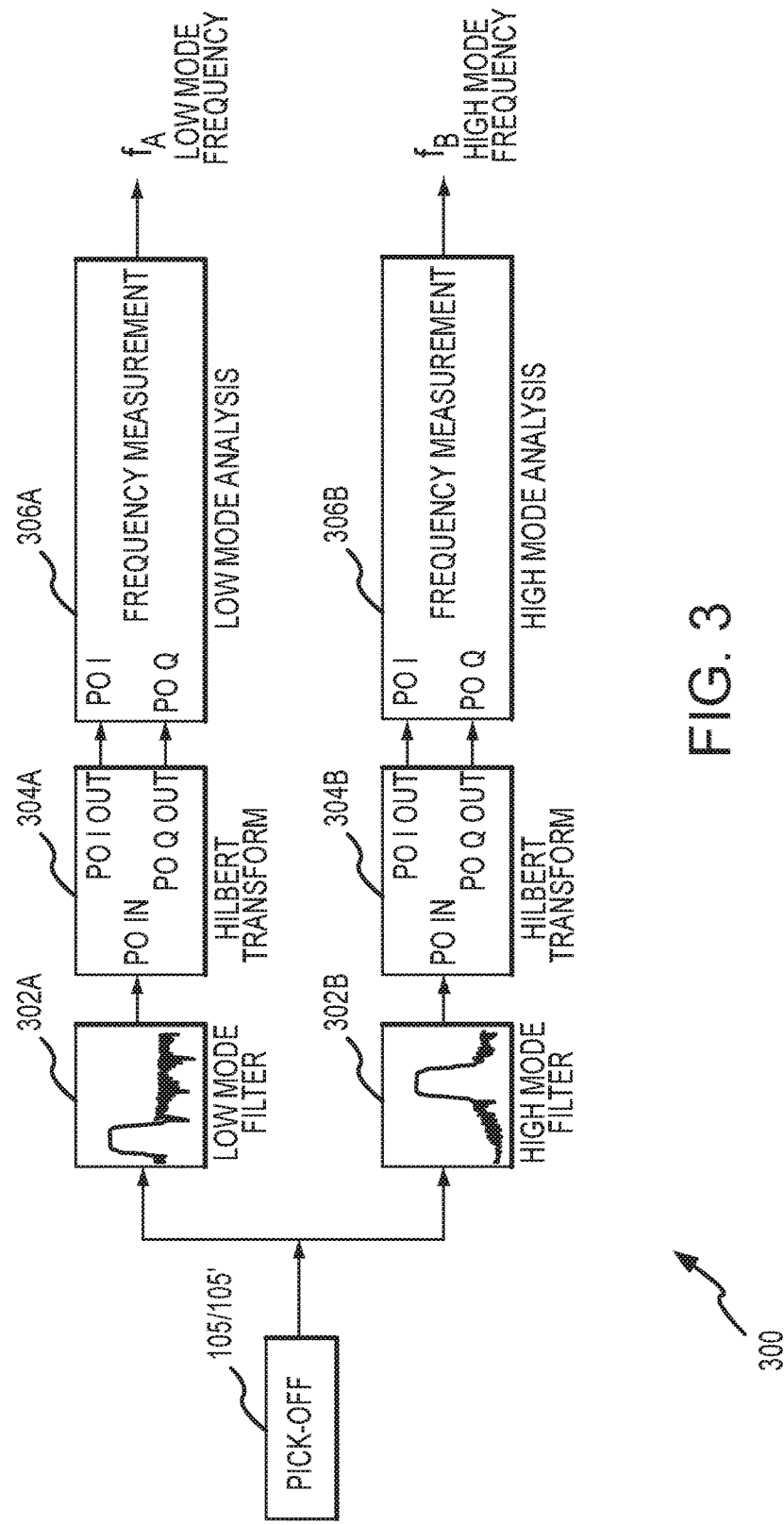
FIG. 3 shows circuitry for generating a first frequency and at least a second frequency according to an embodiment of the invention.

FIG. 3 shows circuitry 300 for generating a first frequency and at least a second frequency according to an embodiment of the invention. This embodiment is used with a single vibratory flow meter and therefore, the circuitry 300 is coupled to a single pick-off 105, 105' of the vibratory flow meter 5. The circuitry 300 can comprise a portion of the meter electronics 20. Alternatively, the circuitry 300 can comprise a portion of a processing system 707 (see FIG. 7 and accompanying discussion). The circuitry 300 includes filters 302A and 302B, Hilbert transforms 304A and 304B, and analysis blocks 306A and 306B.

The filter 302A filters out the first frequency component (i.e., a "low mode" in some embodiments) from the pick-off sensors 105, 105' while the filter 302B filters out the at least second frequency component (i.e., a high frequency mode in some embodiments). The filters 302A and 302B therefore create two separate processing branches. More than two processing branches can be configured if desired, such as if more than two vibrational frequencies are employed.

In one embodiment, the filtering can comprise band-pass filtering centered around the expected fundamental frequency of the flow meter. The filtering can include filtering to remove noise and unwanted signals. In addition, other conditioning operations can be performed, such as amplification, buffering, etc. If the sensor signals comprise analog signals, this block can further comprise any manner of sampling, digitization, and decimation that are performed in order to produce digital sensor signals.

In some embodiments, the mode filters 302A and 302B comprise digital Finite Impulse Response (FIR) polyphase decimation filters. However, it should be understood that the mode filters do not have to comprise FIR filters and therefore the specific filters used should not limit the scope of the present invention. According to an embodiment of the invention, the filters can be implemented in a processing device or processing routine of the meter electronics 20 or the processing system 707. These filters provide an optimal method for filtering and decimating the pick-off sensor signal, with the filtering and decimating being performed at the same chronological time and at the same decimation rate. Alternatively, the filters 302A and 302B can comprise Infinite Impulse Response (IIR) filters or other suitable digital filters or filter processes. However, it should be understood that other filtering processes and/or filtering embodiments are contemplated and are within the scope of the description and claims.

The Hilbert transform 304A phase shifts the first frequency component by about ninety degrees and the Hilbert transform 304B phase shifts the at least second frequency component by about ninety degrees. The phase shifting operation generates I and Q components (i.e., in-phase and quadrature components) of the respective frequency components. However, it should be understood that the 90 degree phase shift can be performed by any manner of phase shift mechanism or operation.

The I and Q components are received and processed by the analysis blocks 306A and 306B. The processing produces the first frequency $f_A$ and at least a second frequency $f_B$. The first frequency $f_A$ and the at least second frequency $f_B$ can be used to generate the first density and the at least second density.

The frequency according to an embodiment of the invention is advantageously computed from the 90 degree phase shift. The frequency in one embodiment uses the 90 degree phase shift and the corresponding sensor signal from which the 90 degree phase shift is derived (i.e., from the I and Q components).

The frequency thus derived is obtained without the need for any independent frequency reference signal. The frequency is obtained from the single 90 degree phase shift in an operation that is very fast. The resulting frequency has a high degree of accuracy.

Figure 4:
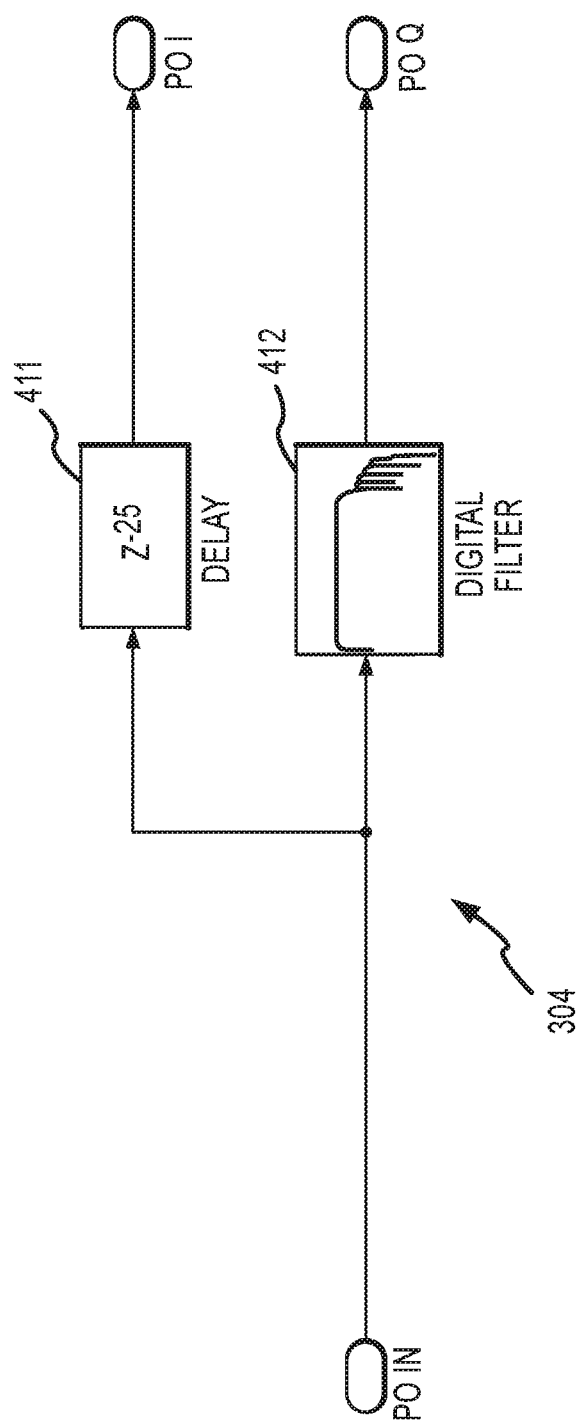
FIG. 4 shows details of a portion of the Hilbert transform blocks according to an embodiment of the invention.

FIG. 4 shows details of a portion of the Hilbert transform blocks 304A and 304B according to an embodiment of the invention. In the embodiment shown, the Hilbert transform blocks 304A and 304B each include a delay block 411 in parallel with a filter block 412. The delay block 411 introduces sampling delays. The delay block 411 therefore selects digital signal samples that are chronologically later in time than the digital signal samples that are filtered in parallel by the filter block 412. The filter block 412 performs a 90 degree phase shift on the inputted digital signal sample.

The Hilbert transform blocks 304A and 304B produced 90 degree phase-shifted versions of the pick-off signals, i.e., they produce a quadrature (Q) component of the original, in-phase (I) signal. The output of the Hilbert transform blocks 304A and 304B therefore provides the new quadrature (Q) components PO Q and PO Q for the first and the at least second vibrational responses, along with the original, in-phase (I) signal components for the first and the at least second vibrational responses.

The inputs to the Hilbert transform block 304A or 304B can be represented as:

$$PO = A_{PO} \cos(\omega t) \quad (13)$$

Using the Hilbert transform the output becomes:

$$PO = A_{PO} \sin(\omega t) \quad (14)$$

Combining the original terms with the output of the Hilbert transform yields:

$$PO = A_{PO}[\cos(\omega t) + i \sin(\omega t)] = A_{PO} e^{j(\omega t)} \quad (15)$$

Figure 5:
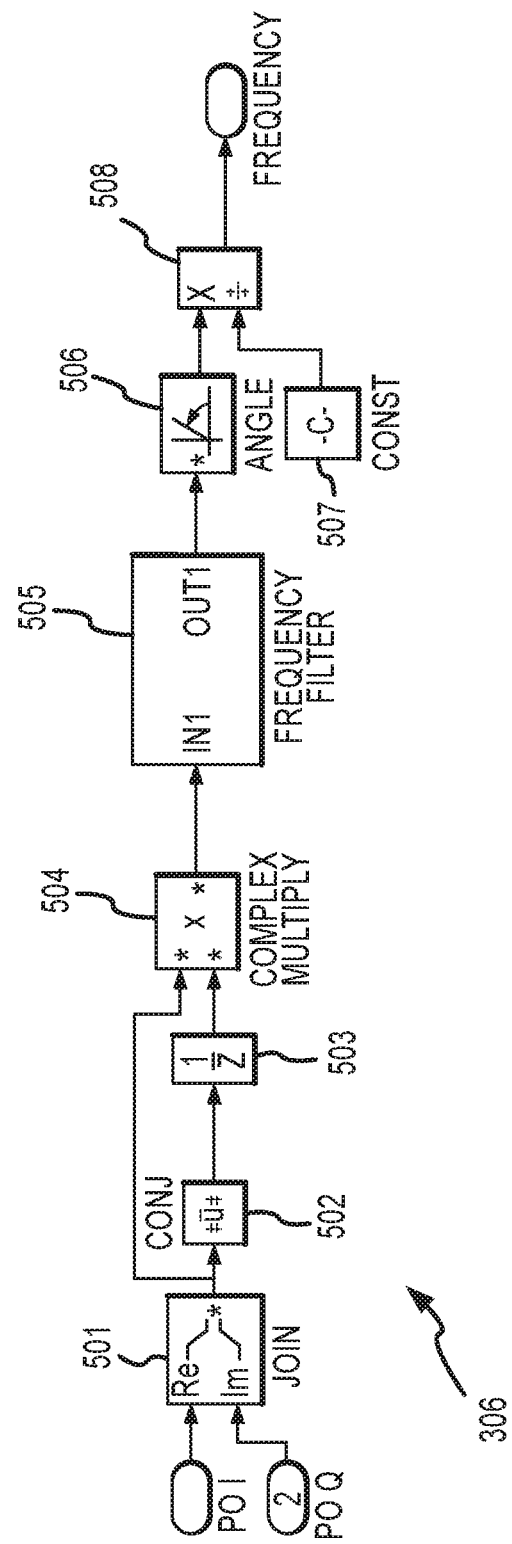
FIG. 5 is a block diagram of the analysis block according to an embodiment of the invention.

FIG. 5 is a block diagram of the analysis block 306A or 306B according to an embodiment of the invention. The analysis block 306A or 306B receives a signal from a single pick-off (PO) signal. The analysis block 306A or 306B in the embodiment shown includes a join block 501, a complex conjugate block 502, a sampling block 503, a complex multiplication block 504, a filter block 505, a phase angle block 506, a constant block 507, and a division block 508.

The join block 501 receives both the in-phase (I) and quadrature (Q) components of a particular vibrational response and passes them on. The conjugate block 502 performs a complex conjugate on the vibrational response and forms a negative of the imaginary signal. The delay block 503 introduces a sampling delay into the analysis block 306A or 306B and therefore selects a digital signal sample that is chronologically older in time. This older digital signal sample is multiplied with the current digital signal in the complex multiplication block 504. The complex multiplication block 504 multiplies the PO signal and the PO conjugate signal, implementing equation (20) below. The filter block 505 implements a digital filter, such as the FIR filter previously discussed. The filter block 505 can comprise a polyphase decimation filter that is used to remove harmonic content from the in-phase (I) quadrature (Q) components of the sensor signal, as well as to decimate the signal. The filter coefficients can be chosen to provide decimation of the inputted signal, such as decimation by a factor of 10, for example. The phase angle block 506 determines a phase angle from the in-phase (I) and quadrature (Q) components of the PO signal. The phase angle block 506 implements a portion of equation (16) below. The constant block 507 supplies a factor comprising a sample rate $F_s$ divided by two pi, as shown in equation 18. The division block 508 performs the division operation of equation 18.

The analysis block 306A or 306B implements the following equation:

$$PO_{n-1} \times PO_n = A_{PO} e^{-j(\omega t_{-1})} \times A_{PO}^2 e^{j(\omega t - \omega t_{-1})} \quad (16)$$

The angle between two consecutive samples is therefore:

$$\omega t - \omega t_{-1} = \tan^{-1}\left[\frac{\sin(\omega t - \omega t_{-1})}{\cos(\omega t - \omega t_{-1})}\right] \quad (17)$$

which is the radian frequency of the vibrational response. Converting to Hz:

$$f_{PO} = \frac{(\omega t - \omega t_{-1}) \times Fs}{2\pi} \quad (18)$$

where "Fs" is the rate of the Hilbert transform block 304A or 304B.

Figure 6:
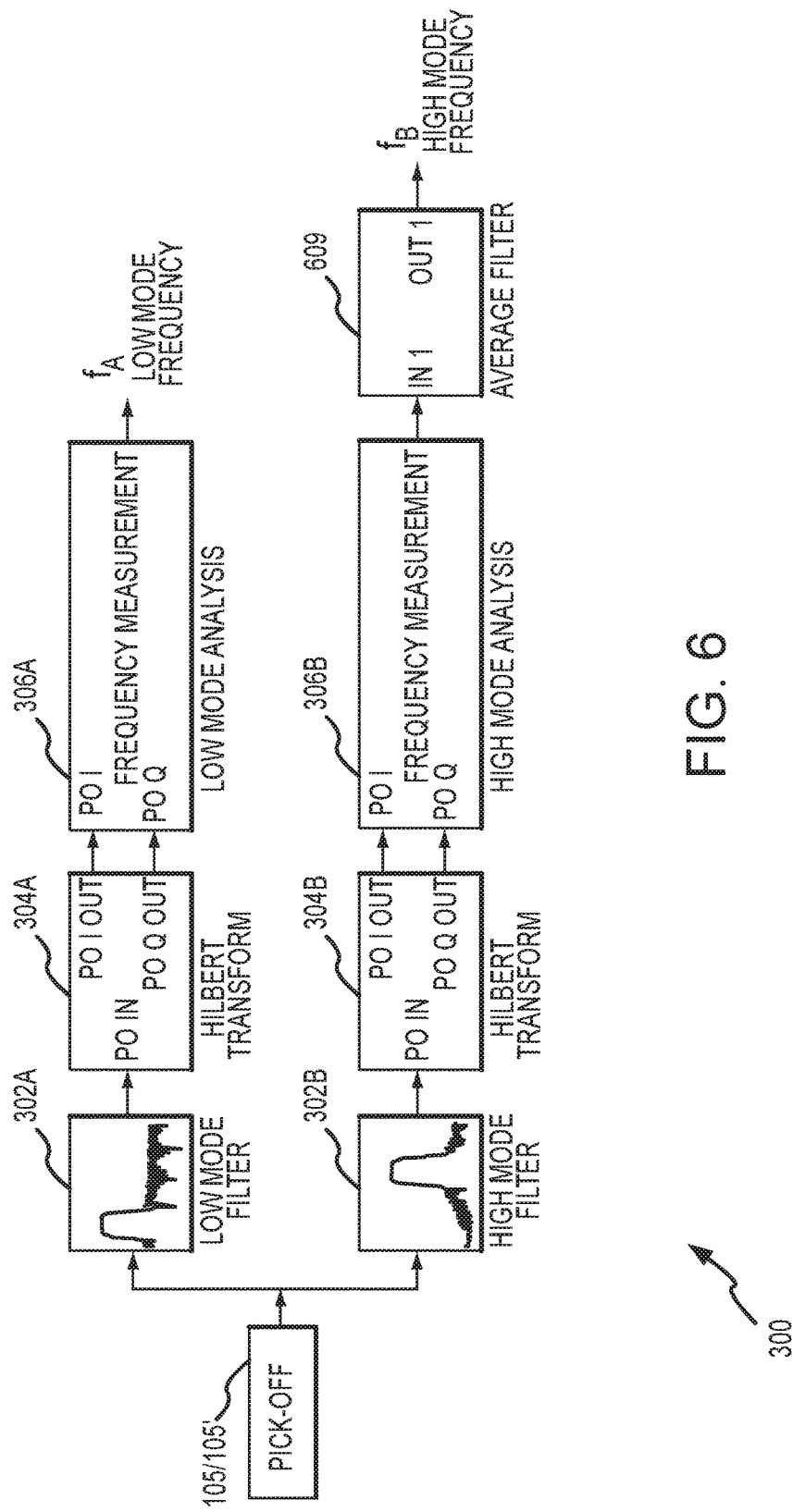
FIG. 6 shows the circuitry for generating a first frequency and at least a second frequency according to an embodiment of the invention.

FIG. 6 shows the circuitry 300 for generating a first frequency and at least a second frequency according to an embodiment of the invention. Components in common with other embodiments share reference numbers. This embodiment differs from the previous embodiment 300 by further including an averaging filter 609.

This embodiment likewise receives a vibrational response from the single pick-off sensor 105, 105'. However, the single vibratory flow meter in this embodiment may be vibrated at only a single frequency, wherein noise in the flow meter generates a second vibrational response, as previously discussed. The circuitry 300 therefore takes advantage of noise in the flow system. Since small amounts of flow noise will stimulate sensor modes, a self-induced higher vibrational response mode will be detectable even if no drive signal is provided. This means only one drive signal is required.

This method requires much more filtering since the higher mode signal (which is not being reinforced with a drive) will be at a much lower amplitude. Because the approximate frequency range of this higher mode vibrational response is known, the lower amplitude is not a significant problem. In addition, another concern is that because of the lower amplitude, the density measurement will be much noisier as well. As long as slower response times are acceptable, this problem can be eliminated by averaging many samples after the frequency measurement has taken place. To this end, the averaging filter 609 can average out the at least second frequency in order to improve the frequency determination and reduce noise and errors in the result.

Figure 7:
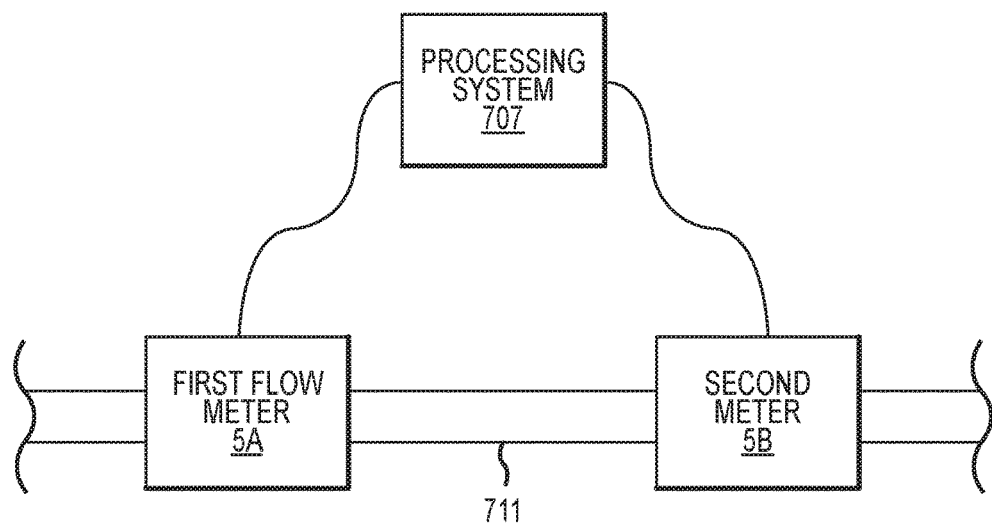
FIG. 7 shows a vibratory flow meter system for calculating a velocity of sound in the fluid flow according to an embodiment of the invention.

FIG. 7 shows a vibratory flow meter system 700 according to another embodiment of the invention. The vibratory flow meter system 700 includes a first flow meter 5A and at least a second flow meter 5B. The flow meters 5A and 5B are connected in a conduit 711. The flow meters 5A and 5B both measure the flowing material flowing in the conduit 711. The processing system 707 is coupled to the first flow meter 5A and the at least second flow meter 5B. The processing system 707 receives a first vibrational response from the first flow meter 5A and receives at least a second vibrational response from the at least second flow meter 5B. The processing system 707 can determine a first density, at least a second density, and a velocity of sound for the flowing material as previously discussed and as discussed below with FIG. 8.

Figure 8:
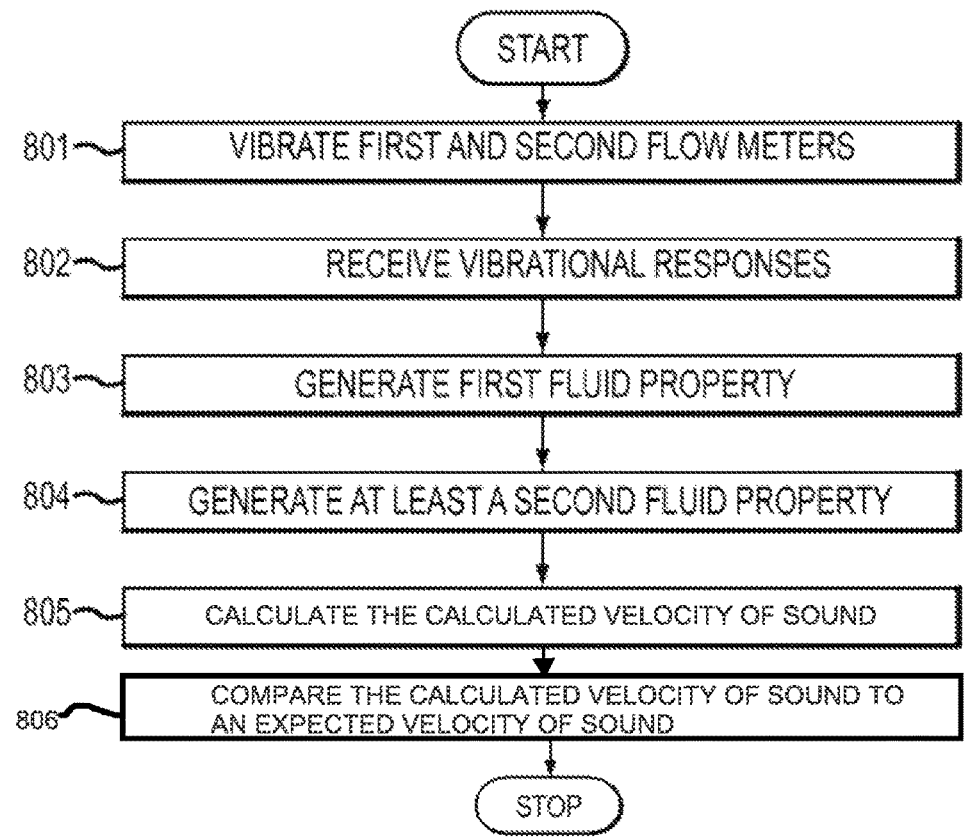
FIG. 8 is a flowchart of a method for calculating a velocity of sound in the fluid flow according to an embodiment of the invention.

FIG. 8 is a flowchart 800 of a method for determining a fluid parameter of a fluid according to an embodiment of the invention. In step 801, a first vibratory flow meter and at least a second vibratory flow meter are vibrated. The first vibratory flow meter is vibrated at a first frequency and generates a first vibrational response. The at least second vibratory flow meter is vibrated at an at least second frequency and generates an at least second vibrational response.

Two or more vibratory flow meters are employed according to this embodiment of the invention. It should be understood that more than two vibratory flow meters can be included and more than two vibrational responses can be received. Multiple vibrational responses can be employed and may further refine the fluid parameter calculations.

In step 802, the first vibrational response and the at least second vibrational response are received from the first vibratory flow meter and the at least second vibratory flow meter. The at least second vibrational response comprises a different frequency than the first vibrational response, as previously discussed.

In step 803, a first fluid property is generated, as previously discussed.

In step 804, at least a second fluid property is generated, as previously discussed.

In step 805, a fluid parameter of the flowing fluid is calculated based on the first fluid property and the at least second fluid property, as previously discussed.

The above described invention allows a user/operator of a vibratory meter to calculate various fluid parameters. The calculation can be performed based on a vibrational response. The vibrational response may include at least a first and at least a second frequency component. The first and at least second frequency component may be a result of vibrating the flow meter at multiple frequencies. Alternatively, the first and at least second frequency component may be a result of vibrating the flow meter at a single frequency. Therefore, the present invention does not require the use of separate acoustic meters to measure the velocity of sound as required in the prior art. Furthermore, in some embodiments, the present invention can calculate a velocity of sound with only a single flow meter.

The calculated velocity of sound may be used in a number of different ways as discussed above. It should be appreciated that the implementations discussed above are merely examples to emphasize the utility of the present invention and in no way should it limit the scope of the present invention. Rather, the present invention's applicability is much greater than the limited examples discussed above.

The detailed descriptions of the above embodiments are not exhaustive descriptions of all embodiments contemplated by the inventors to be within the scope of the invention. Indeed, persons skilled in the art will recognize that certain elements of the above-described embodiments may variously be combined or eliminated to create further embodiments, and such further embodiments fall within the scope and teachings of the invention. It will also be apparent to those of ordinary skill in the art that the above-described embodiments may be combined in whole or in part to create additional embodiments within the scope and teachings of the invention.

Thus, although specific embodiments of, and examples for, the invention are described herein for illustrative purposes, various equivalent modifications are possible within the scope of the invention, as those skilled in the relevant art will recognize. The teachings provided herein can be applied to other vibratory meters, and not just to the embodiments described above and shown in the accompanying figures. Accordingly, the scope of the invention should be determined from the following claims.

We claim:

1. A method for calculating a velocity of sound of a fluid flowing through at least a first vibratory flow meter, comprising the steps of:
   vibrating the flow meter at one or more frequencies;
   receiving a vibrational response;
   generating a first fluid property of the fluid;
   generating at least a second fluid property of the fluid based on the vibrational response;
   determining an expected fluid property;
   comparing a difference between the first fluid property and an expected fluid property to a threshold value to determine if the first fluid property is an actual fluid property;
   determining a method of calculating the velocity of sound based on whether the first fluid property is the actual fluid property; and
   calculating the velocity of sound based on the first fluid property and the at least second fluid property using the determined method.

2. The method of claim 1, wherein the first fluid property comprises a first density measurement and the at least second fluid property comprises at least a second density measurement.

3. The method of claim 1, wherein the first fluid property comprises a first mass flow rate and the at least second fluid property comprises at least a second mass flow rate.

4. The method of claim 1, wherein the step of vibrating the vibratory flow meter comprises the steps of:
   vibrating the vibratory flow meter at a first frequency; and
   further vibrating the vibratory flow meter at an at least second frequency, with the at least second frequency being a different frequency than the first frequency.

5. The method of claim 1, further comprising the step of separating the vibrational response into a first frequency component of the vibrational response and an at least second frequency component of the vibrational response.

6. The method of claim 1, wherein the first fluid property is based on a first frequency component of the vibrational response and the at least second fluid property is based on an at least second frequency component of the vibrational response.

7. The method of claim 1, wherein the step of vibrating the vibratory flow meter comprises the steps of:
   vibrating the vibratory flow meter at a first frequency; and
   separating the vibrational response into a first frequency component and an at least second frequency component, wherein the first frequency component and the at least second frequency component are generated by the vibration at the first frequency.

8. The method of claim 1, further comprising the steps of:
   vibrating at least a second vibratory flow meter;
   generating the first fluid property from the first vibratory flow meter; and
   generating the at least second fluid property from the at least second vibratory flow meter.

9. The method of claim 8, wherein the steps of vibrating the first flow meter and the at least second flow meter comprises the steps of:
   vibrating the first flow meter at a first frequency; and
   vibrating the at least second flow meter at an at least second frequency, with the at least second frequency being different than the first frequency.

10. The method of claim 1, wherein the first fluid property and at least second fluid property comprises a first density measurement and at least a second density measurement and wherein the first density measurement is generated from a known fluid density.

11. The method of claim 1, wherein the first fluid property and at least second fluid property comprises a first density measurement and at least a second density measurement and further comprising the steps of:
comparing the first density measurement to an expected density measurement; and
if the difference between the first density measurement and the expected density measurement is less than a threshold value, determining that the first density measurement comprises an actual fluid density.

12. The method of claim 1, wherein the first fluid property and the at least second fluid property comprises a first mass flow rate and at least a second mass flow rate and further comprising the steps of:
comparing the first mass flow rate to an expected mass flow rate; and
if the difference between the first mass flow rate and the expected mass flow rate is less than a threshold value, determining that the first mass flow rate comprises the actual mass flow rate.

13. The method of claim 1, wherein the first fluid property and at least second fluid property comprises a first density measurement and at least a second density measurement and further comprising the steps of:
comparing the first density measurement to an expected density; and
if the difference between the first density measurement and the expected density measurement exceeds a threshold value calculating an actual density.

14. The method of claim 1, wherein the first fluid property and at least second fluid property comprises a first mass flow rate and at least a second mass flow rate and further comprising the steps of:
comparing the first mass flow rate to an expected mass flow rate; and
if the difference between the first mass flow rate and the expected mass flow rate exceeds a threshold value calculating an actual mass flow rate.

15. The method of claim 1, further comprising the step of calculating a density error based on the calculated velocity of sound.

16. The method of claim 15, further comprising the step of correcting the density based on the calculated density error.

17. The method of claim 1, further comprising the step of calculating a mass flow error based on the calculated velocity of sound.

18. The method of claim 17, further comprising the step of correcting a mass flow rate based on the calculated mass flow error.

19. A vibratory flow meter (5) for calculating a velocity of sound of a flowing fluid, comprising a meter assembly (10) including vibratory sensors (104, 105, 105') and meter electronics (20) coupled to the vibratory sensors, with the vibratory flow meter (5) being characterized by:
the meter electronics (20) being configured to:
receive a vibrational response from the vibratory sensors;
generate a first fluid property of the fluid;
generate at least a second fluid property of the fluid based on the vibrational response;
determine an expected fluid property;
compare a difference between the first fluid property and an expected fluid property to a threshold value to determine if the first fluid property is an actual fluid property;
determine a method of calculating the velocity of sound based on whether the first fluid property is the actual fluid property;
calculate the velocity of sound based on the first fluid property and the at least second fluid property using the determined method.

20. The vibratory flow meter (5) of claim 19, wherein the first fluid property comprises a first density measurement and at least second fluid property comprises at least a second density measurement.

21. The vibratory flow meter (5) of claim 19, wherein the first fluid property comprises a first mass flow rate and the at least second fluid property comprises at least a second mass flow rate.

22. The vibratory flow meter (5) of claim 19, wherein the first fluid property is based on a first frequency component of the vibrational response and the at least second fluid property is based on at least a second frequency component of the vibrational response.

23. The vibratory flow meter (5) of claim 19, with the meter electronics (20) being further configured to vibrate the vibratory flow meter (5) at a first frequency and at an at least second frequency, with the at least second frequency being a different frequency than the first frequency.

24. The vibratory flow meter (5) of claim 19, with the meter electronics (20) being further configured to separate the vibrational response into a first frequency component and an at least second frequency component.

25. The vibratory flow meter (5) of claim 19, with the meter electronics (20) being further configured to vibrate the flow meter at a first frequency and separate the vibrational response into a first frequency component and an at least second frequency component, wherein the first frequency component and the at least second frequency component are generated by the vibration at the first frequency.

26. The vibrator flow meter (5) of claim 19, wherein the first fluid property and at least second fluid property comprises a first density measurement and at least a second density measurement wherein the first density measurement is generated from a known fluid density.

27. The vibratory flow meter (5) of claim 19, wherein the first fluid property and at least second fluid property comprises a first density measurement and at least a second density measurement and with the meter electronics (20) being further configured to compare the first density measurement to an expected density and if the difference between the first density measurement and the expected density is less than a threshold value, determine that the first density measurement comprises an actual density.

28. The vibratory flow meter (5) of claim 19, wherein the first fluid property and at least second fluid property comprises a first mass flow rate and at least a second mass flow rate and with the meter electronics (20) being further configured to compare the first mass flow rate to an expected mass flow rate and if the difference between the first mass flow rate and the expected mass flow rate is less than a threshold value, determine that the first mass flow rate comprises an actual mass flow rate.

29. The vibratory flow meter (5) of claim 19, with the meter electronics (20) being further configured to calculate a density error based on the calculated velocity of sound.

30. The vibratory flow meter (5) of claim 29, with the meter electronics (20) being further configured to correct a density based on the density error.

31. The vibratory flow meter (5) of claim 19, with the meter electronics (20) being further configured to calculate a mass flow error based on the calculated velocity of sound.

32. The vibratory flow meter (5) of claim 31, with the meter electronics (20) being further configured to correct a mass flow rate based on the mass flow error.

33. A vibratory flow meter system (700) for calculating a fluid parameter of a flowing fluid, comprising a first flow meter (5A) and at least a second flow meter (5B) and a processing system (707) coupled to the first flow meter (5A) and the at least second flow meter (5B), with the vibratory flow meter system (700) being characterized by:
the processing system (701) being configured to:
receive a first vibrational response from the first flow meter (5A) and receive at least a second vibrational response from the at least second flow meter (5B);
generate a first fluid property of the fluid;
generate at least a second fluid property of the fluid based on the at least second vibrational response;
determine an expected fluid property;
compare a difference between the first fluid property and an expected fluid property to a threshold value to determine if the first fluid property is an actual fluid property;
determine a method of calculating the velocity of sound based on whether the first fluid property is the actual fluid property; and
calculate a velocity of sound based on the first fluid property and the at least second fluid property.

34. The vibratory flow meter system (700) of claim 33, wherein the first fluid property comprises a first density measurement and at least second fluid property comprises at least a second density measurement.

35. The vibratory flow meter system (700) of claim 33, wherein the first fluid property comprises a first mass flow rate and the at least second fluid property comprises at least a second mass flow rate.

36. The vibratory flow meter system (700) of claim 33, with the processing system (701) being further configured to vibrate the first flow meter (5A) at a first frequency and vibrate the at least second flow meter (5B) at an at least second frequency, with the at least second frequency being different than the first frequency.

37. The vibratory flow meter system (700) of claim 33, wherein the first fluid property and at least second fluid property comprises a first density measurement and at least a second density measurement and wherein the first density measurement is generated from a known fluid density.

38. The vibratory flow meter system (700) of claim 33, wherein the first fluid property and at least second fluid property comprises a first density measurement and at least a second density measurement and with the processing system (701) being further configured to:
compare the first density measurement to an expected density measurement; and
determine that the first density measurement comprises an actual fluid density if the difference between the first density measurement and the expected density measurement is less than a threshold value.

39. The vibratory flow meter system (700) of claim 33, wherein the first fluid property and at least second fluid property comprises a first density measurement and at least a second density measurement and with the processing system (701) being further configured to:
compare the first density measurement to an expected density; and
calculate an actual density and a velocity of sound of the fluid if the difference between the first density measurement and the expected density measurement exceeds a threshold value.

40. The vibratory flow meter system (700) of claim 33, wherein the first fluid property and at least second fluid property comprises a first mass flow rate and at least a second mass flow rate and with the processing system (701) being further configured to:
compare the first mass flow rate to an expected mass flow rate; and
determine that the first mass flow rate comprises an actual mass flow rate if the difference between the first mass flow rate and the expected mass flow rate is less than a threshold value.

41. The vibratory flow meter system (700) of claim 33, wherein the first fluid property and at least second fluid property comprises a first mass flow rate and at least a second mass flow rate and with the processing system (701) being further configured to:
compare the first mass flow rate to an expected mass flow rate; and
calculate an actual mass flow rate and a velocity of sound of the fluid if the difference between the first mass flow rate and the expected mass flow rate exceeds a threshold value.

42. The vibratory flow meter system (700) of claim 33, with the processing system (701) being further configured to calculate a density error based on the calculated velocity of sound.

43. The vibratory flow meter system (700) of claim 42, with the processing system (701) being further configured to correct a density based on the calculated density error.

44. The vibratory flow meter system (700) of claim 33, with the processing system (701) being further configured to calculate a mass flow error based on the calculated velocity of sound.

45. The vibratory flow meter system (700) of claim 44, with the processing system (701) being further configured to correct a mass flow rate based on the calculated mass flow error.

* * * * *

UNITED STATES PATENT AND TRADEMARK OFFICE
CERTIFICATE OF CORRECTION

PATENT NO. : 10,466,087 B2
APPLICATION NO. : 13/124192
DATED : November 5, 2019
INVENTOR(S) : Joel Weinstein, Mark James Bell and Andrew Timothy Patten Page 1 of 1

It is certified that error appears in the above-identified patent and that said Letters Patent is hereby corrected as shown below:

On the Title Page

Item (73) Assignee:
Replace "Micron Motion, Inc." with --Micro Motion, Inc.--

In the Specification

Delete Column 15, Lines 10 thru 16 and insert the following:
--In step 206, the calculated velocity of sound for the fluid is compared to an expected velocity of sound. Advantageously, only one calculation needs to be made in order to perform the diagnostic discussed above.--

Column 19, Line 24, insert the following paragraph:
--In step 806, a calculated velocity of sound is compared to an expected velocity of sound, as previously discussed.--

Signed and Sealed this
Sixteenth Day of June, 2020

Andrei Iancu
*Director of the United States Patent and Trademark Office*